(12) United States Patent
Chevalier et al.

(10) Patent No.: US 8,889,296 B2
(45) Date of Patent: Nov. 18, 2014

(54) ACTIVE MATERIAL OF A NICKEL-CADMIUM GENERATOR NEGATIVE ELECTRODE

(75) Inventors: Stéphanie Chevalier, Bordeaux (FR); Claudette Audry, Bruges (FR); Mélanie Dendary, Eysines (FR); Philippe Desprez, Bordeaux (FR); Björn Marlid, Oskarshamn (SE); Rune Sjövall, Sodra Sandly (SE); Jerry Gottfridsson, Oskarshamn (SE)

(73) Assignee: Saft Groupe SA, Bagnolet (FR)

( * ) Notice: Subject to any disclaimer, the term of this patent is extended or adjusted under 35 U.S.C. 154(b) by 733 days.

(21) Appl. No.: 13/141,807

(22) PCT Filed: Dec. 23, 2009

(86) PCT No.: PCT/IB2009/055936
§ 371 (c)(1),
(2), (4) Date: Sep. 12, 2011

(87) PCT Pub. No.: WO2010/073227
PCT Pub. Date: Jul. 1, 2010

(65) Prior Publication Data
US 2011/0318636 A1 Dec. 29, 2011

(30) Foreign Application Priority Data
Dec. 24, 2008 (FR) ..................... 08 07446

(51) Int. Cl.
| H01M 10/24 | (2006.01) |
| H01M 10/30 | (2006.01) |
| H01M 4/24 | (2006.01) |
| H01M 4/04 | (2006.01) |
| B05D 5/12 | (2006.01) |
| H01M 4/48 | (2010.01) |
| C07F 15/04 | (2006.01) |
| C07C 53/10 | (2006.01) |

(52) U.S. Cl.
CPC ............... H01M 4/246 (2013.01); H01M 4/48 (2013.01); H01M 2300/0014 (2013.01); Y02E 60/124 (2013.01); H01M 10/30 (2013.01); C07F 15/045 (2013.01); C07C 53/10 (2013.01)
USPC ..... 429/222; 429/223; 429/218.1; 252/182.1; 427/126.1; 29/623.1

(58) Field of Classification Search
USPC ................... 429/218.1, 222, 223; 252/182.1; 427/126.1; 29/623.1
See application file for complete search history.

(56) References Cited

U.S. PATENT DOCUMENTS

| 3,837,919 A | 9/1974 | Gutrdige |
| 4,983,477 A | 1/1991 | Takemura et al. |

FOREIGN PATENT DOCUMENTS

| JP | 58-198856 A | 11/1983 |
| JP | 3-238755 A | 10/1991 |
| WO | 00/69005 A1 | 11/2000 |

*Primary Examiner* — Carlos Barcena
(74) *Attorney, Agent, or Firm* — Sughrue Mion, PLLC

(57) ABSTRACT

The hydration of cadmium oxide in the presence of nickel acetate gives the possibility of obtaining a compound of general formula $Cd_{1-x}Ni_x(OH)_{2-y}(CH_3CO_2)_y$, with $0<x\leq0.05$ and $0<y\leq0.10$. This compound may be advantageously, used as an electrochemically active material of an anode of the envelope type of a nickel cadmium generator. This anode does not contain any sulfates responsible for the formation of short-circuits. Further, this anode has a high electrochemical yield. A method for preparing this compound and the anode is described.

15 Claims, 4 Drawing Sheets

ACTIVE MATERIAL OF A NICKEL-CADMIUM GENERATOR NEGATIVE ELECTRODE

CROSS-REFERENCE TO RELATED APPLICATIONS

Figure 1:
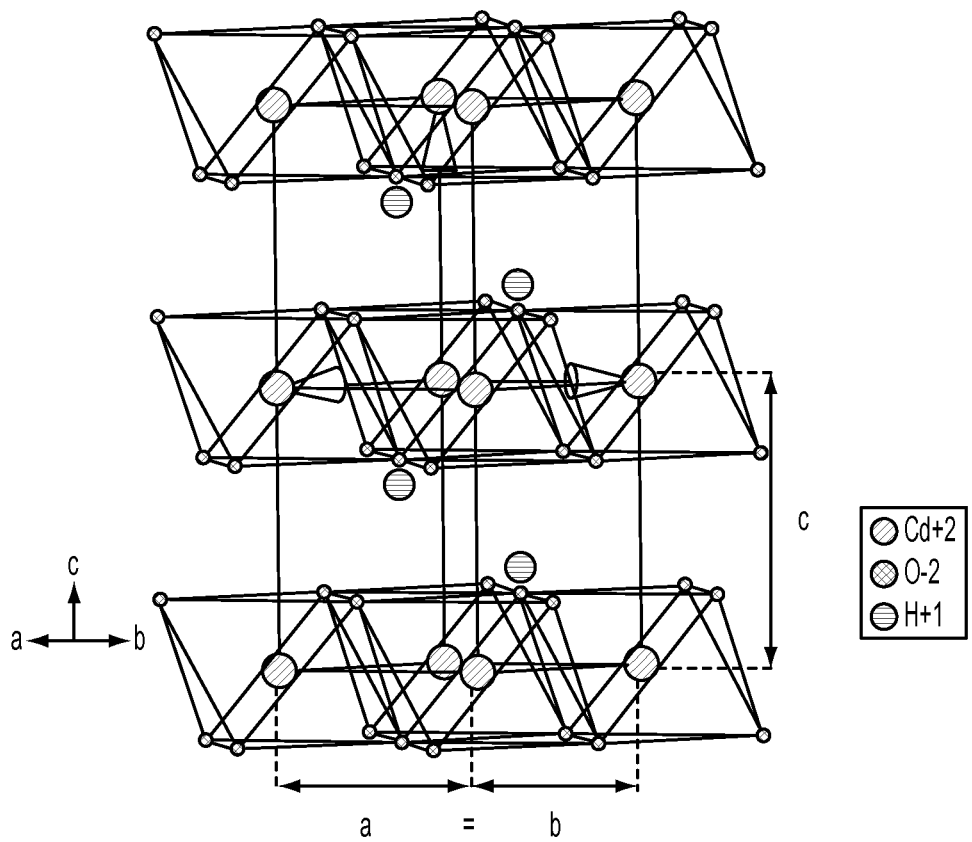

This application is a National Stage of International Application No. PCT/IB2009/055936 filed Dec. 23, 2009, claiming priority based on French Patent Application No. 0807446, filed Dec. 24, 2008, the contents of all of which are incorporated herein by reference in their entirety.

TECHNICAL FIELD

The technical field to which relates the invention is that of electrochemically active materials which may be used in the negative electrode of a nickel-cadmium type electrochemical generator also called nickel-cadmium type accumulator.

STATE OF THE ART

An electrochemical generator of the nickel-cadmium type generally comprises one or more positive electrodes or cathode(s) containing an electrochemically active material based on nickel hydroxide as well as one or more negative electrodes or anode(s) containing an electrochemical active material based on cadmium oxide. At least one separator, generally of polyolefin or polyamide, is inserted between a positive electrode and a negative electrode. The positive, negative electrodes and the separator are introduced into a container and then impregnated with an electrolyte which is a concentrated solution of a strong base selected from KOH, LiOH, NaOH or a mixture of the latter.

The negative cadmium electrode of this type of generator may be made according to several methods.

In a first method, a nickel sintered porous support is alternately soaked in solutions of a cadmium salt and of soda, allowing the filling of the pores of the sintered material with cadmium hydroxide which is the negative active material of the accumulator. This technique allows good volume distribution of the active material and good collection of the current, whence strong power. This electrode, a so-called « cadmium sintered electrode » has the drawback of being expensive.

In a second method, cadmium oxide CdO powder is mixed with different additives (conductives, stabilizers). To this mixture is added an aqueous solution containing a binder so as to obtain a slurry. The stabilizer limits the hydration reaction of CdO into $Cd(OH)_2$ to 10-20%. The obtained slurry is deposited on a current conductor support in order to obtain an electrode. The current collector support is generally a deployed metal or a perforated nickel steel sheet. The electrode is then dried. The obtained electrode is a so-called « pasted electrode », « slurried electrode » or « plasticized electrode ». This method is the most used for small nickel-cadmium accumulators intended for portable applications or for industrial accumulators for applications of the cycling type. This method is inexpensive and lends itself to mass productions but with it, it is not possible to obtain accumulators with a very long lifetime, for example 15-20 years.

In a third method, cadmium oxide CdO powder is mixed with different conducting additives and a binder allowing agglomeration of the powders. The powders are mixed and water added with nickel sulfate is added. A slurry is obtained wherein cadmium oxide is in majority hydrated (hydration level of more than 60%). This slurry is dried and introduced into perforated sleeves in nickel steel sheets which are assembled for forming the electrodes. A detailed description of this third « electrode envelope » method is found for example in chapter 26 of the reference text book « Handbook of batteries » of David Linden published by McGraw-Hill in 1994 (ISBN 0-07-037921-1).

Such a technical solution however has the drawback of causing internal short-circuits to the generator. Indeed, the residual sulfates in the negative electrode are salted out into the electrolyte and migrate towards the positive electrode, causing swelling of the latter. The swelling increases the pressure inside the envelope electrode which has the consequence of outflow of a portion of the carbon conducting additive added to the positive active material. Sulfate ions of the electrolyte, when their concentration exceeds about $1.7 \times 10^{-2}$ mol·$L^{-1}$ (equivalent to 3 g·$L^{-1}$ of $K_2SO_4$) are also responsible for the formation of $K_2SO_4$ crystals. (S. Uno FALK, Alvin J. SALKIND, Alkaline storage batteries, John Wiley and Sons, 1969). These crystals covered with conducting carbon are responsible for the formation of internal short-circuits. The use of nickel sulfate as an agent for hydrating cadmium oxide CdO therefore either imposes washing of the negative electrodes for removing the residual sulfates, or a change of electrolyte in the container of the battery.

An electrochemically active material is therefore sought for a negative « envelope electrode » of a nickel cadmium accumulator having improved initial electrochemical yield and good cycling stability. Minimization of the risks of internal short-circuits related to the use of this electrochemically active material is also desired. In this way, the steps for washing the negative electrodes and changing the electrolyte may be suppressed.

SUMMARY OF THE INVENTION

For this purpose, the object of the invention is a compound of formula $Cd_{1-x}Ni_x(OH)_{2-y}(CH_3CO_2)_y$, with $0<x\leq0.05$ and $<y\leq0.10$.

According to an embodiment, this compound crystallizes in the beta form.

According to an embodiment, the compound in the beta crystalline form has a lattice parameter « a » comprised between 3.485 Å and 3.495 Å.

According to an embodiment, $x\geq0.01$, preferably $x\geq0.02$, advantageously $x\geq0.035$.

The object of the invention is also an electrochemically active material comprising the compound described above, and the electrode comprising said electrochemically active material.

In a preferred embodiment, the electrode is of the envelope type.

The object of the invention is also an electrochemical generator with an alkaline electrolyte, at least one negative electrode of which is an electrode as described earlier. Preferably, the electrochemical generator is of the nickel-cadmium type.

According to an embodiment, the generator has an initial electrochemical capacity greater than 250 mAh/g at room temperature, for 7 h 30 min charging under C/5 conditions, discharging under C/5 conditions, and a cut-off voltage of 0.8V.

According to an embodiment, the sulfate ion concentration in the electrolyte is less than about $5.7\times10^{-3}$ mol·$L^{-1}$.

The object of the invention is also a method for preparing the compound described above, this method comprises the following steps:
(i) reaction of cadmium oxide powder with an aqueous solution of nickel acetate, (ii) drying the thereby obtained mixture, and
(iii) optionally additional hydration.

According to an embodiment, the method comprises an additional compression step after the drying step (ii) or after the additional hydration step (iii).

The object of the invention is also a method for preparing an electrode, comprising the following steps:
(i') reaction of a cadmium oxide powder with an aqueous solution of nickel acetate,
(ii') drying the thereby obtained mixture,
(iii') compression of the dry mixture,
(iv') depositing the compressed mixture on a current collector in order to obtain an electrode, and
(v') exposing the obtained electrode to an aqueous solution.

The invention also aims at a method for preparing an « envelope electrode », the electrochemically active material of which comprises the compound according to the invention.

SHORT DESCRIPTION OF THE FIGURES

FIG. 1 is a schematic illustration of the compact hexagonal crystalline structure of $\beta$-Cd(OH)$_2$.

Figure 2:
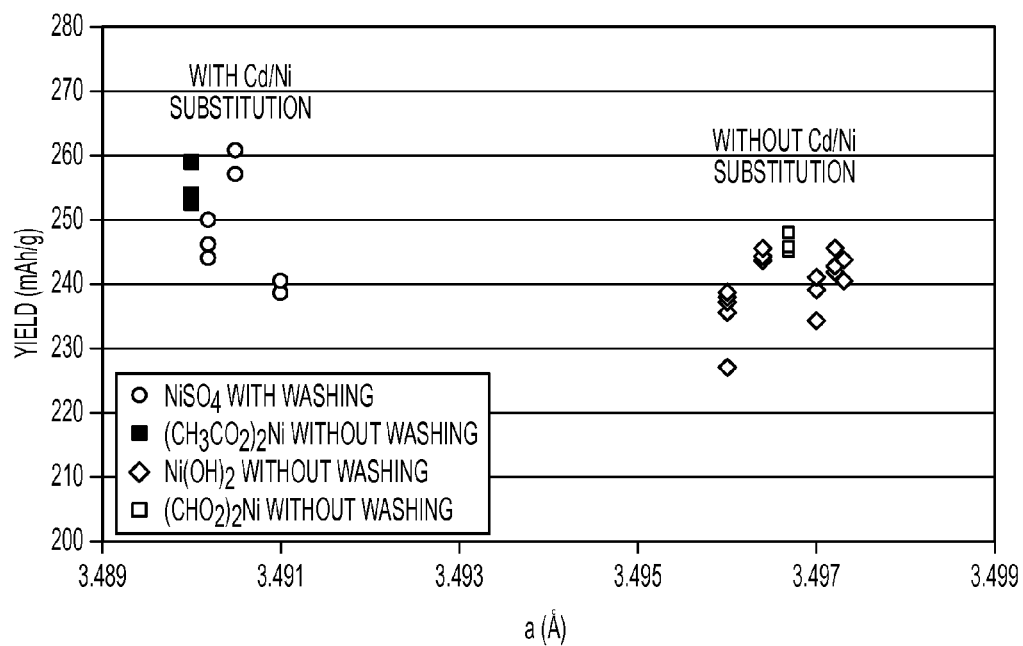

FIG. 2 illustrates the electrochemical yield (mAh/g) of the electrochemically active material according to the invention, versus the value of the lattice cell parameter a (Å), for different additives used during hydration.
Ex.1: NiSO$_4$ with washing of the electrodes or changing the electrolyte;
Ex.2: Ni(CH$_3$CO$_2$)$_2$ without washing;
Ex.3: Ni(OH)$_2$ with washing;
Ex.4: Ni(CHO$_2$)$_2$ with washing.
In the examples of FIG. 2, the percentage of the number of nickel moles based on the total number of nickel and cadmium moles is 1.9 mol %.

Figure 3:
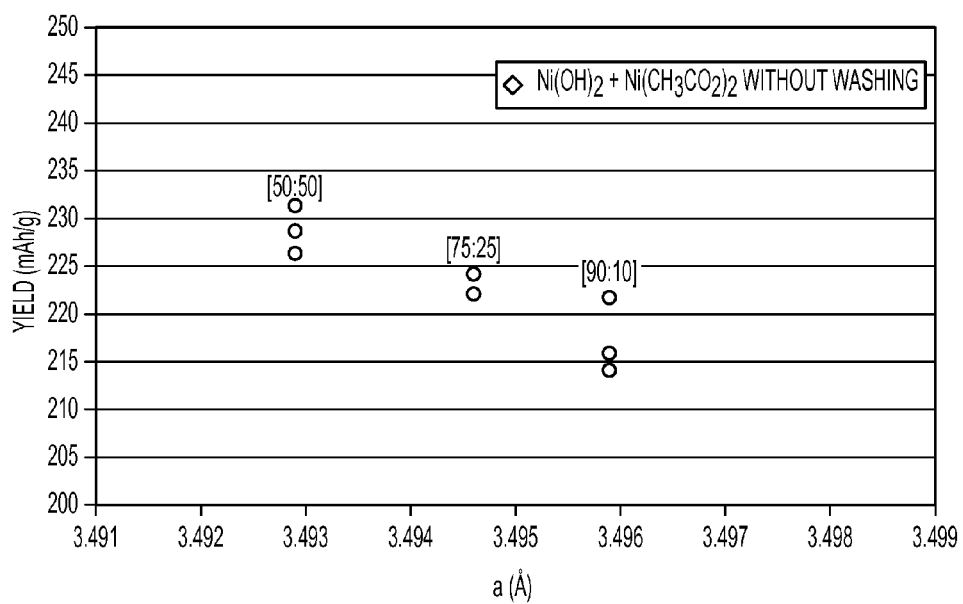

FIG. 3 illustrates the electrochemical yield (mAh/g) of the electrochemically active material according to the invention, versus the value of the lattice cell parameter a (Å), for the mixture of two additives Ni(OH)$_2$ and Ni(CH$_3$CO$_2$)$_2$ without washing the electrode. The indications [50:50], [75:25] and [90:10] represent the mass ratio of Ni(OH)$_2$ and Ni(CH$_3$CO$_2$)$_2$. The percentage of the total number of nickel moles based on the total number of nickel and cadmium moles is 2.8 mol %.

Figure 4:
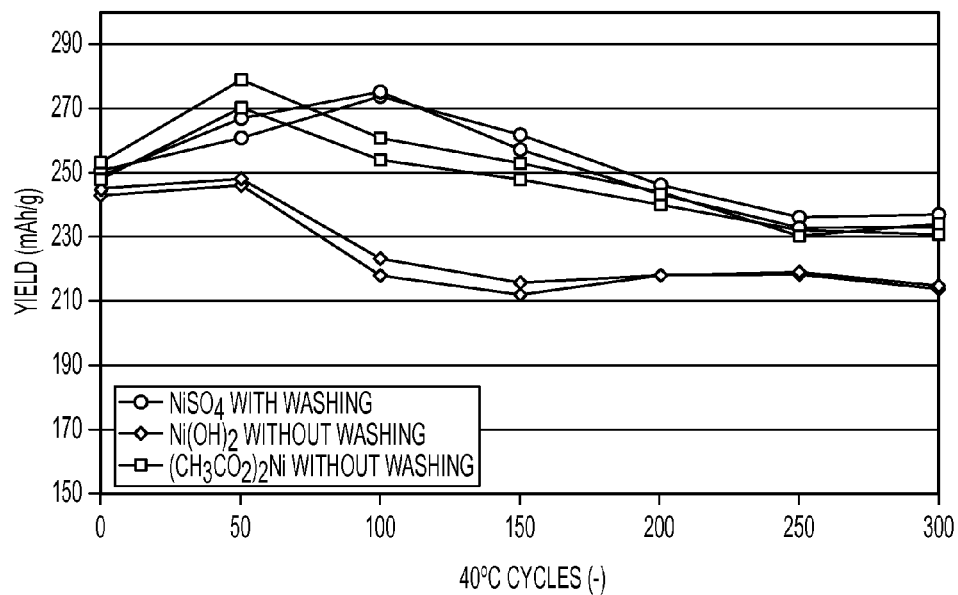

FIG. 4 illustrates the change in the electrochemical yield (mAh/g) at 40° C. of the electrochemically active material according to the invention versus the number of performed cycles, for different additives used during the hydration.

DETAILED DESCRIPTION OF THE EMBODIMENTS

The invention is based on the use of an active material based on cadmium hydroxide obtained by a method comprising a step for hydrating the cadmium oxide in the presence of an additive which is nickel acetate Ni(CH$_3$CO$_2$)$_2$. During the hydration step, the cadmium oxide CdO is transformed into cadmium hydroxide Cd(OH)$_2$. The use of nickel acetate during hydration gives the possibility of obtaining an active material having an improved initial electrochemical yield while minimizing the risks of short-circuits. By initial electrochemical yield is meant the electrochemical yield of the negative active material after formation and before cycling. The electrochemical formation includes a charge-discharge cycle, the charging phase being performed at room temperature under C/5 conditions for 12 h 30 min and the discharging phase is performed at the same temperature under C/5 conditions down to 0.8V.

During the hydration phase of cadmium oxide, a portion of the cadmium ions of the cadmium hydroxide is replaced with nickel ions. This substitution is possible since nickel acetate is soluble in an aqueous solution and may co-precipitate at the same time as the cadmium in the hydration phase. Also, during hydration, a portion of the hydroxide ions of cadmium hydroxide is replaced with acetate ions. A portion of the acetate ions may also be inserted between the cadmium sheets. The hydration reaction of cadmium oxide in the presence of nickel acetate allows formation of the compound Cd$_{1-x}$Ni$_x$(OH)$_{2-y}$(CH$_3$CO$_2$)$_y$, with 0<x≤0.05 and 0<y≤0.10.

According to a preferred embodiment, the compound Cd$_{1-x}$Ni$_x$(OH)$_{2-y}$(CH$_3$CO$_2$)$_y$, with 0<x≤0.05 and 0<y≤0.10 of the invention crystallizes in the $\beta$ phase. The crystalline $\beta$ phase is characterized by a hexagonal lattice as illustrated in FIG. 1 in the case of $\beta$-Cd(OH)$_2$. The structure is of the brucite type. It is characterized by three unit cell parameters a=b and c. The volume of the unit cell is given by the relationship: $V = a^2 \times c \times \sin 60°$.

The determination of the lattice cell parameter may be achieved by X-ray diffraction (XRD). The radiation used is: Cu K$\alpha$ (1.54065 Å). The lattice parameters of the hydroxide $\beta$-Cd$_{1-x}$Ni$_x$(OH)$_{2-y}$(CH$_3$CO$_2$)$_y$ are refined by means of the structural refinement software package TOPAS R (Rietveld method for powders) from Bruker AXS. In addition to $\beta$-Cd$_{1-x}$Ni$_x$(OH)$_{2-y}$(CH$_3$CO$_2$)$_y$, this software package allows simulation of the whole of the other phases present in the mixture: CdO, $\gamma$-Cd(OH)$_2$ for the cadmium derivatives as well as for the annex phases (additives). The corrections related to the displacement of the sample in the beam are taken into account. The refinement is conducted on 13 lines, up to the line (2 0 2) towards 75° in 2θ. The measurement step is 0.03° and the counting time is from 1.5 to 2' per step.

The incorporation of nickel into the crystalline lattice of cobalt hydroxide has the effect of reducing the value of the unit cell parameter « a » which passes from a value comprised between about 3.495 to 3.499 Å for $\beta$-Cd(OH)$_2$ to a value comprised between 3.485 Å to 3.495 Å for $\beta$-Cd$_{1-x}$Ni$_x$(OH)$_{2-y}$(CH$_3$CO$_2$)$_y$. By selecting this range of values for the lattice cell parameter it is possible to obtain an active material having a high yield. The lattice cell parameter « a » of this active material depends on the partial substitution level of cadmium by nickel. The lattice cell parameter « a » follows a linear time-dependent change law between the pure $\beta$-Cd(OH)$_2$ phase and the pure $\beta$-Ni(OH)$_2$ phase. This is Vegard's law which is experimentally verified. From this relationship, it is possible to calculate the substitution level x of Cd by Ni in the (3-Cd(OH)$_2$ lattice as a function of « a ».

$$x(\%) \approx (3.496 - a)/0.0031$$

The tests have shown that the maximum substitution level x is of about 5%.

According to an embodiment, x is greater than or equal to 0.01.

According to an embodiment, x is greater than or equal to 0.02.

According to an embodiment, x is greater than or equal to 0.035.

The method for making the compound according to the invention comprises the following steps:
a) a cadmium oxide powder is provided;
b) to the cadmium oxide powder are added optional additives improving electron conductivity of the active material such as nickel metal powder, carbon black. Organic binders as well as additives of the transition metal oxide type are also added;

c) an aqueous solution of nickel acetate is prepared. Preferably the nickel acetate concentration is comprised between 0.1 and 1 mol·L$^{-1}$;

d) the aqueous solution of step c) is added to the mixture of step b). The added amount of solution is adjusted so as to obtain a mixture having the consistency of a slurry. The step for putting the aqueous solution into contact with the cadmium oxide is the step for prehydrating cadmium oxide;

e) the slurry is left to rest for a period of at least about 12 hours at room temperature.

In this step, the cadmium oxide is already almost quasi-hydrated into cadmium hydroxide (the hydration level of cadmium oxide is greater than 90%).

The slurry of step e) is dried in order to remove water and to obtain a powder. The powder is compressed, which then assumes the shape of a brick. This brick is placed between two current collector plates which may be perforated metal sheets. This is referred to as an « envelope assembly» . The thereby obtained electrode is inserted into the container of the generator. The latter is filled with electrolyte. The contact between the cadmium oxide and the electrolyte of the generator causes termination of the hydration of the cadmium oxide into cadmium hydroxide.

The advantage of the nickel acetate hydration additives is to minimize the risk of internal short-circuits without washing the negative electrode, while providing electrochemical yields equivalent to those obtained with nickel sulfate. This improvement in the electrochemical yields is related to the partial substitution of Cd by Ni in the β-Cd(OH)$_2$ lattice, obtained for nickel sulfate and nickel acetate additives.

The invention relates to all electrochemical generators with an alkaline electrolyte, at least one negative electrode of which is based on cadmium. It particularly applies to electrochemical generators of the nickel cadmium type with « envelope electrodes» .

EXAMPLES

Different active cadmium materials were made by using different hydration additives. In all the examples, the ratio of the number of nickel moles over the total number of nickel and cadmium moles: Ni/(Ni+Cd) is 1.9 mol %.

Example 1

Not According to the Invention

The hydration additive used is nickel hydroxide Ni(OH)$_2$. Ni(OH)$_2$ is an insoluble compound. So no substitution of cadmium of the cadmium hydroxide by the nickel element is observed. The lattice cell parameter « a» has a value from 3.496 to 3.497 Å. The obtained initial electrochemical yield is less than 250 mAh/g. (FIG. 2 and Table 1)

Example 2

According to the Invention

The hydration additive used is nickel acetate Ni(CH$_3$CO$_2$)$_2$. In an aqueous solution, dissolution of nickel acetate is observed. The nickel ions from nickel acetate are substituted for the cadmium of cadmium hydroxide. By X-ray diffraction a reduction in the lattice cell parameter « a» is seen, which is located in the range from 3.490 to 3.491 Å. The initial electrochemical yield is greater than 250 mAh/g (FIG. 2 and Table 1). No washing of the electrodes or change of electrolyte are required.

Example 3

Not According to the Invention

The hydration additive used is nickel sulfate Ni(SO$_4$). In an aqueous solution, dissolution of nickel sulfate is observed. The nickel ions from the nickel sulfate are substituted for cadmium of the cadmium hydroxide: The lattice cell parameter « a» has a value of 3.490 to 3.491 Å. The residual sulfate ions in the active material are responsible for the formation of internal short circuits. It is therefore necessary to carry out washing of the electrodes or a change of electrolyte (FIG. 2 and Table 1).

Example 4

Not According to the Invention

The hydration additive used is nickel formate Ni(CHO$_2$)$_2$. In an aqueous solution, very low dissolution of nickel formate is observed. So no substitution of the cadmium of cadmium hydroxide by the nickel element is observed. The lattice cell parameter « a» has the value of 3.497 Å (FIG. 2 and Table 1)

FIG. 4 shows a nickel cadmium generator, at least one negative electrode of which contains as an electrochemically active material, the compound according to the invention, has a high initial electrochemical capacity, of at least 250 mAh/g of negative active material. Such a generator also has good cycling performances since the yield after 150 cycles is of about 250 mAh/g. On the contrary, the generator for which at least one negative electrode contains as an electrochemically active material, a compound prepared by pre-hydration with a solution containing Ni(OH)$_2$, has an electrochemical capacity of less than 250 mAh/g.

Table 1 takes up again the results illustrated in FIG. 2 and additionally indicates the initial hydration level of the cadmium oxide CdO before assembling it into an « envelope electrode» .

TABLE 1

| Hydration Agent | Initial CdO hydration level (%) | Lattice cell parameter « a» of β-Cd(OH)$_2$ (Å) | Electrochemical capacity (mAh · g$^{-1}$) |
|---|---|---|---|
| NiSO$_4$ | 97 | 3.491 | 240.4 |
| | | | 238.6 |
| | | | 238.6 |
| | 87 | 3.491 | 257.2 |
| | | | 261.0 |
| | 94 | 3.490 | 250.2 |
| | | | 246.3 |
| | | | 244.0 |
| Ni(OH)$_2$ | 89 | 3.496 | 235.7 |
| | | | 238.7 |
| | | | 227.1 |
| | 82 | 3.496 | 238.0 |
| | | | 237.3 |
| | 90 | 3.497 | 239.4 |
| | | | 234.3 |
| | | | 241.3 |
| | 84 | 3.497 | 242.9 |
| | | | 241.9 |
| | | | 245.6 |
| | 74 | 3.496 | 243.9 |
| | | | 245.7 |
| | | | 244.4 |
| | 82 | 3.497 | 240.6 |
| | | | 243.9 |

TABLE 1-continued

| Hydration Agent | Initial CdO hydration level (%) | Lattice cell parameter «a» of β-Cd(OH)$_2$ (Å) | Electrochemical capacity (mAh · g$^{-1}$) |
|---|---|---|---|
| Ni(CH$_3$CO$_2$)$_2$ | 95 | 3.490 | 258.9 |
|  | 96 | 3.490 | 252.7 |
|  |  |  | 253.8 |
| Ni(CHO$_2$)$_2$ | 94 | 3.497 | 245.1 |
|  |  |  | 246.2 |
|  |  |  | 248.1 |

The invention claimed is:

1. A compound of formula Cd$_{1-x}$Ni$_x$(OH)$_{2-y}$(CH$_3$CO$_2$)$_y$ with 0<x≤0.05 and 0<y≤0.10.

2. The compound according to claim 1, in the crystalline beta form.

3. The compound according to claim 2, having a lattice cell parameter «a» comprised between 3.485 Å and 3.495 Å.

4. The compound according to claim 1, wherein x≥0.01.

5. The compound according to claim 1, wherein x≥0.02.

6. The compound according to claim 1, wherein x≥0.035.

7. An electrode comprising an active material which is the compound according to claim 1.

8. The electrode according to claim 7, wherein the electrode is configured as an envelope.

9. An electrochemical generator with an alkaline electrolyte for which at least one electrode is an electrode according to claim 7.

10. The electrochemical generator according to claim 9, wherein a sulfate ion concentration in the electrolyte is less than about 5.7×10$^{-3}$ mol·L$^{-1}$.

11. The electrochemical generator according to claim 9, of the nickel cadmium type.

12. A method for preparing a compound of formula Cd$_{1-x}$Ni$_x$(OH)$_{2-y}$(CH$_3$CO$_2$)$_y$ with 0<x≤0.05 and 0<y≤0.10, comprising the following steps:
   (i) reaction of cadmium oxide powder with an aqueous solution of nickel acetate,
   (ii) drying of the thereby obtained mixture, and
   (iii) optionally additional hydration.

13. The method according to claim 12, comprising an additional compression step after the drying step (ii) or after the additional hydration step (iii).

14. The preparation method according to claim 12, wherein the compound is of formula Cd$_{1-x}$Ni$_x$(OH)$_{2-y}$(CH$_3$CO$_2$)$_y$, with 0<x≤0.05 and 0<y≤0.10.

15. A method for preparing an electrode, comprising the following steps:
   (i') reacting cadmium oxide powder with an aqueous solution of nickel acetate,
   (ii') drying the thereby obtained mixture,
   (iii') compressing the dry mixture,
   (iv') depositing the compressed mixture on a current collector in order to obtain an electrode and,
   (v') exposing the obtained electrode to an aqueous solution.

* * * * *